United States Patent
Kast et al.

(10) Patent No.: US 9,629,996 B2
(45) Date of Patent: Apr. 25, 2017

(54) LEAD HAVING RADIALLY SPACED APART CONTACTS TO ALLOW FOR ADJUSTABILITY

(71) Applicant: MEDTRONIC, INC., Minneapolis, MN (US)

(72) Inventors: John E. Kast, Hugo, MN (US); James A. Zimmerman, Blaine, MN (US); Craig S. Pilarski, Ham Lake, MN (US); William C. Phillips, Brooklyn Park, MN (US); Thomas I. Miller, Blaine, MN (US); Mary L. Boatright, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 165 days.

(21) Appl. No.: 14/212,019

(22) Filed: Mar. 14, 2014

(65) Prior Publication Data

US 2014/0200642 A1 Jul. 17, 2014

Related U.S. Application Data

(62) Division of application No. 12/992,922, filed as application No. PCT/US2009/045577 on May 29, 2009, now Pat. No. 8,676,320.

(Continued)

(51) Int. Cl.
*A61N 1/05* (2006.01)
*A61N 1/375* (2006.01)
(Continued)

(52) U.S. Cl.
CPC ............. *A61N 1/0551* (2013.01); *A61N 1/05* (2013.01); *A61N 1/3752* (2013.01);
(Continued)

(58) Field of Classification Search
CPC .. A61B 2562/227; A61N 1/05; A61N 1/0529; A61N 1/0534; A61N 1/0551;
(Continued)

(56) References Cited

U.S. PATENT DOCUMENTS 5,082,453 A * 1/1992 Stutz, Jr. .............. A61N 1/3752
439/265
7,174,219 B2 2/2007 Wahlstrand
(Continued)

FOREIGN PATENT DOCUMENTS

WO WO 00/64535 11/2000

*Primary Examiner* — Amanda Patton
(74) *Attorney, Agent, or Firm* — Mueting, Raasch & Gebhardt, P.A.

(57) ABSTRACT

An implantable medical lead includes a lead body having a proximal portion and a distal portion. The lead also includes first and second contacts located at the proximal portion of the lead body, and includes first and second electrodes located at the distal portion of the lead body. The first electrode is electrically coupled to the first contact and the second electrode is electrically coupled to the second contact. The first contact has a proximal end and a distal end and the second contact has proximal end and a distal end. The second contact is radially spaced apart from the first contact. The contacts do not extend around the lead body. This disclosure also relates to an implantable lead extension and to an implantable signal generator having connectors configured to receive the present lead.

9 Claims, 9 Drawing Sheets

Related U.S. Application Data

(60) Provisional application No. 61/058,292, filed on Jun. 3, 2008, provisional application No. 61/175,481, filed on May 5, 2009.

(51) Int. Cl.
    *H01R 24/58*       (2011.01)
    *H01R 107/00*     (2006.01)

(52) U.S. Cl.
    CPC ....... *A61B 2562/227* (2013.01); *A61N 1/0529* (2013.01); *A61N 1/0534* (2013.01); *H01R 24/58* (2013.01); *H01R 2107/00* (2013.01); *H01R 2201/12* (2013.01)

(58) Field of Classification Search
    CPC .............. A61N 1/3752; H01R 2107/00; H01R 2201/12; H01R 24/58
    See application file for complete search history.

(56) References Cited

U.S. PATENT DOCUMENTS

| | | |
|---|---|---|
| 7,286,882 B2 | 10/2007 | Cole |
| 2004/0093051 A1 | 5/2004 | Chinn |
| 2004/0267328 A1 | 12/2004 | Duffin |

\* cited by examiner

LEAD HAVING RADIALLY SPACED APART CONTACTS TO ALLOW FOR ADJUSTABILITY

This is a divisional application of U.S. patent application Ser. No. 12/992,922, filed Nov. 16, 2010, which application claims the benefit of and is a U.S. National Stage filing under 35 U.S.C. 371 of copending PCT Application Serial No. PCT/US09/45577, filed May 29, 2009, which in turn claims the benefit of U.S. Provisional Application No. 61/058,292, filed Jun. 3, 2008 "Lead Having Radially Spaced Apart Contacts to Allow for Adjustability", and U.S. Provisional Application No. 61/175,481, filed May 5, 2009, "Lead Having Radially Spaced Apart Contacts to Allow for Adjustability," the disclosures of which are incorporated herein by reference in their entirety.

FIELD

The present disclosure relates to implantable medical devices; more particularly to medical leads having radially spaced apart proximal contacts.

BACKGROUND

Headaches, such as migraines, and occipital neuralgia are often incapacitating and may lead to significant consumption of drugs to treat the symptoms. However, a rather large number of people are unresponsive to drug treatment, leaving them to wait out the episode or to resort to coping mechanisms. For refractive occipital neuralgia, nerve ablation or separation may effectively treat the pain.

Occipital nerve stimulation may serve as an alternative for treatment of migraines or occipital neuralgia. For example, a dual channel implantable electrical generator may be implanted subcutaneously in a patient. A distal portion of first and second leads may be implanted in proximity to a left and right occipital nerve such that one or more electrode of the leads are in electrical communication with the occipital nerves. The proximal portions of the leads may then be connected to the signal generator such that electrical signals can be delivered from the signal generator to the electrodes to apply therapeutic signals to the occipital nerves Alternatively, two single channel implantable electrical generators may be employed, where the first lead is connected to one signal generator and the second lead is connected to the second signal generator. In either case, the lead is typically tunneled subcutaneously from the site of implantation of the signal generator to the occipital nerve or around the base of the skull. Such tunneling can be time consuming and is invasive.

It may be desirable to reduce the amount of tunneling by placing the electrical signal generator in close proximity to the location of the nerve to be stimulated. Another way to reduce tunneling may be to tunnel a single lead extension having a distal end capable of receiving more than one lead to a location close to the nerves to be stimulated, and then coupling the leads to the extension. In either case, the implanted distance that the lead spans is greatly reduced.

For applications where nerves in the head are to be stimulated, it may be desirable to minimize or eliminate excess lead length. Typically leads are longer than needed to allow a given lead model or configuration to be used for a variety of purposes and in patients of varying size. Excess lead is typically wrapped or coiled in a subcutaneous pocket in which the electrical signal generator is implanted. However, in some areas of the body, such as under the scalp, coiling or wrapping of excess lead length may be uncomfortable for the patient in which the lead is implanted or may cause lead abrasion due to, e.g., rubbing against the skull.

BRIEF SUMMARY

The present disclosure, among other things, describes leads having elongate radially spaced apart contacts that allow for adjustment of the length of the lead extending from an implantable medical device. Such adjustability may be sufficient to allow the lead to be properly placed during an implant procedure or may allow the lead to be used for patients with differing anatomical sizes. Such adjustability may also allow for the elimination of excess coiled lead, particularly when the lead is configured to extend only a short distance from the medical device to which the lead is configured to be coupled. Such leads may be beneficial for applying electrical stimulation signals to occipital nerves, particularly when the leads are connected to a lead extension or signal generator in proximity to the occipital nerves.

In an embodiment of this disclosure, an implantable medical lead is described. The lead includes a lead body having a proximal portion and a distal portion. The lead also includes first and second contacts located at the proximal portion of the lead body, and includes first and second electrodes located at the distal portion of the lead body. The first electrode is electrically coupled to the first contact, and the second electrode is electrically coupled to the second contact. The first contact has a proximal end and a distal end, and the second contact has proximal end and a distal end. The second contact is radially spaced apart from the first contact. Lead extensions and implantable signal generators having connectors for receiving such a lead are also described. The distance that the lead extends from such the extension or signal generator may be adjusted by axial movement of the lead relative to the device, due to the configuration of the contacts of the lead.

In an embodiment, a method for adjusting the distance from which a lead extends from a face of a connector configured to receive the lead is described. The connector includes a lead receptacle having first and second internal contacts configured to electrically couple to first and second contacts of a lead having elongate radially spaced apart contacts. The method includes inserting the lead having elongate radially spaced apart contacts into the lead receptacle and adjusting the distance that the lead extends from the face of the connector by axially moving the lead within the lead receptacle. The first and second contacts of the lead are capable of electrically coupling to the first and second internal contacts of the receptacle as the lead is being axially moved within the receptacle.

In an embodiment, a lead has a proximal portion having an elongate contact, and a distal portion having an electrode. The electrode is electrically coupled to the contact. The proximal portion of the lead has a lead body, and the contact does not extend around the lead body.

The leads, extensions, signal generators, systems and methods described herein provide one or more advantages over prior leads, extensions, signal generators, systems and methods. Such advantages will be readily understood from the following detailed description when read in conjunction with the accompanying drawings.

Figure 1:
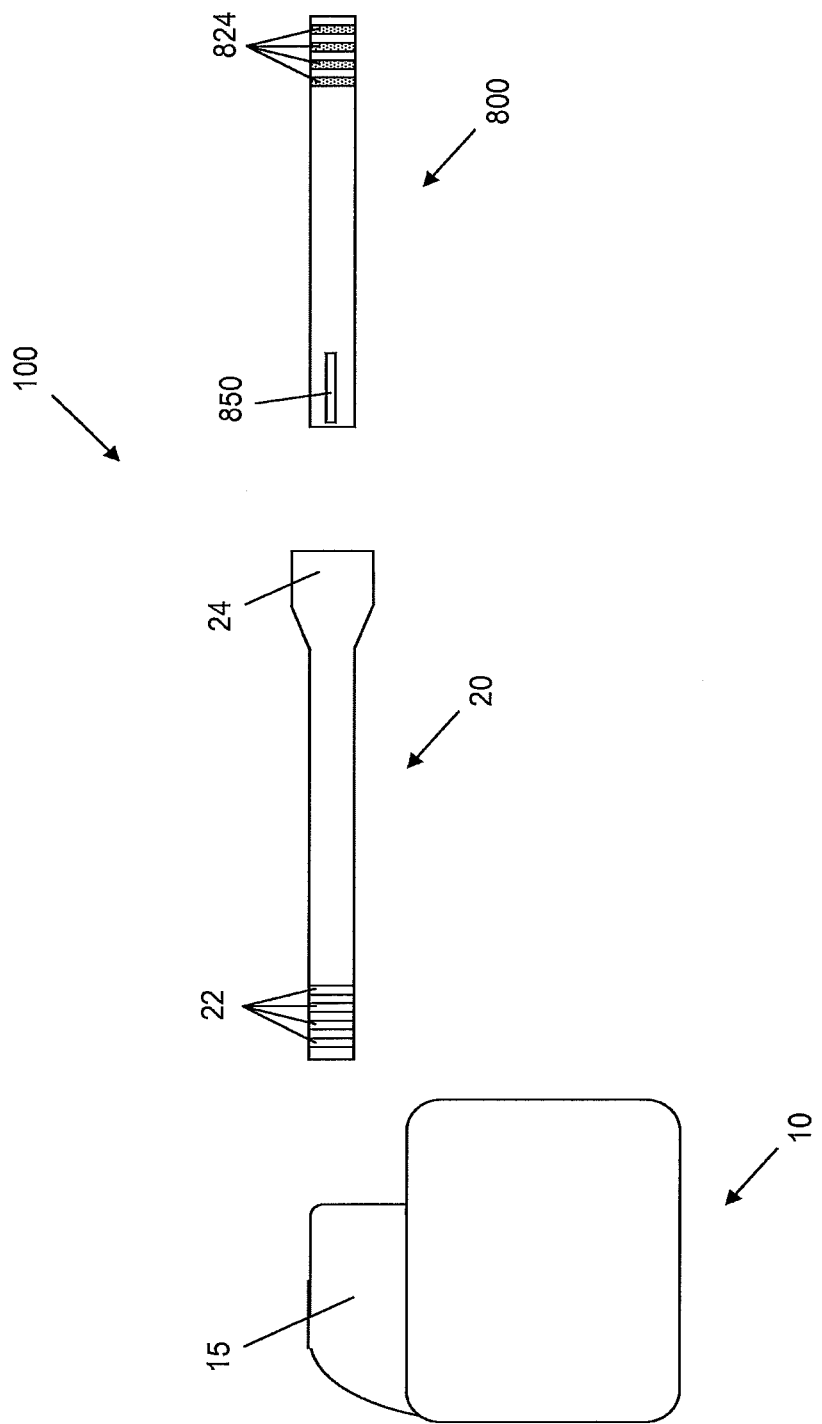
FIG. 1 is a schematic side view of an implantable system including a signal generator, lead extension and lead.

The drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to".

"Exemplary" or "representative" is used in the sense of "for example" or "for the purpose of illustration", and not in a limiting sense.

The present disclosure describes, inter alia, leads having elongate radially spaced apart contacts that allow for adjustment of the length of the lead extending from an implantable medical device. Such leads and associated medical devices, such as lead extensions or signal generators, configured to receive such leads, may, in some circumstances, allow for the leads to be implanted without having to coil or bunch up excess lead length. For example, when the lead is coupled to the signal generator or extension in proximity to the location in which the lead exerts its effect, the lead may be configured to extend only a short distance from the device and minor adjustments in lead placement may be effectuated by adjusting the distance the lead extends from the device.

Nearly any implantable medical device or system employing leads may be used in conjunction with the leads described herein. Representative examples of such implantable medical devices include hearing implants, cochlear implants; sensing or monitoring devices; signal generators such as cardiac pacemakers or defibrillators, neurostimulators (such as spinal cord stimulators, brain or deep brain stimulators, peripheral nerve stimulators, vagal nerve stimulators, occipital nerve stimulators, subcutaneous stimulators, etc.), gastric stimulators; or the like. For purposes of occipital nerve stimulation, electrical signal generators such as Medtronic, Inc.'s Restore® or Synergy® series of implantable neurostimulators may be employed.

Referring to FIG. 1, a schematic side view of a representative electrical signal generator system 100 is shown. In the depicted system 100, the electrical signal generator 10 includes a connector header 15 configured to receive a proximal portion of lead extension 20. The proximal portion of lead extension 20 contains a plurality of electrical contacts 22 that are electrically coupled to internal contacts (not shown) at distal connector 24 of lead extension 20. The connector header 15 of the signal generator 10 contains internal contacts (not shown) and is configured to receive the proximal portion of the lead extension 20 such that the internal contacts of the connector header 15 may be electrically coupled to the contacts 22 of the lead extension 20 when the lead extension 20 in inserted into the header 15.

The system depicted in FIG. 1 further includes a lead 800. The depicted lead 800 has a proximal portion that includes a plurality of contacts 850 (only one shown) and a distal portion that includes a plurality of electrodes 824. Each of the electrodes 824 may be electrically coupled to a discrete contact 850. The distal connector 24 of the lead extension 20 is configured to receive the proximal portion of the lead 800 such that the contacts 850 of the lead 800 may be electrically coupled to the internal contacts of the connector 24 of the extension 20. Accordingly, a signal generated by the signal generator 10 may be transmitted to a patient by an electrode 824 of lead 800 when lead is connected to extension 20 and extension 20 is connected to signal generator 10.

Figure 2:
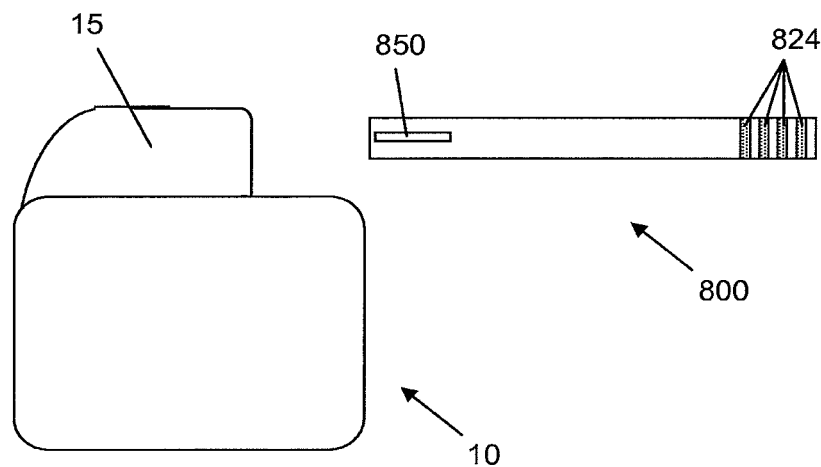
FIG. 2 is a schematic side view of an implantable system including a signal generator and lead.

It will be understood that lead 800 may be coupled to signal generator 10 without use of an extension 20, and the connector header 15 or other lead connector of the signal generator may be configured to make an electrical connection with the contacts 850 of the lead 800 (see, e.g., FIG. 2). Any number of leads 800 or extensions 20 may be coupled to signal generator 10. Typically, one or two leads 800 or extensions 20 are coupled to signal generator 10. While lead 800 is depicted as having four electrodes 824, it will be understood that lead 800 may include any number of electrodes 824, e.g. one, two, three, four, five, six, seven, eight, sixteen, thirty-two, or sixty-four. Corresponding changes in the number of contacts 850 in lead 800, contacts 22 and internal contacts in connector 24 of lead extension, or internal contacts in connector 15 of signal generator 10 may be required or desired.

The leads 800 depicted in FIGS. 1-2 have contacts 850 that are radially spaced apart and allow for adjustability within a connector; e.g., a connector of a lead extension, signal generator, or the like. Leads having such contacts and connectors for receiving such leads are described below in more detail.

Referring now to FIGS. 3A-D, various views of a lead 800 and associated connector 900 (which may be a connector 24 of a lead extension 20 or a connector header 15 of an active implantable medical device; e.g. as shown in FIG. 1) are shown. As shown in the top view of FIG. 3A, the lead 800 includes a lead body 870 proximal portion 872 and a distal portion 874. One or more electrodes 824 are located at the distal portion 874 of the lead body 870. One or more contacts 850 are located at the proximal portion 872 of the lead body 870. By "located at", with regard to an electrode or a contact in relationship to a lead body, it is meant that the electrode or contact is fixed relative to the stated position to the lead body. An electrode or contact located at a specified portion of a lead body, may, with regard to the lead body, be disposed on, disposed partially in, integrally formed with, or the like.

Figure 3A:
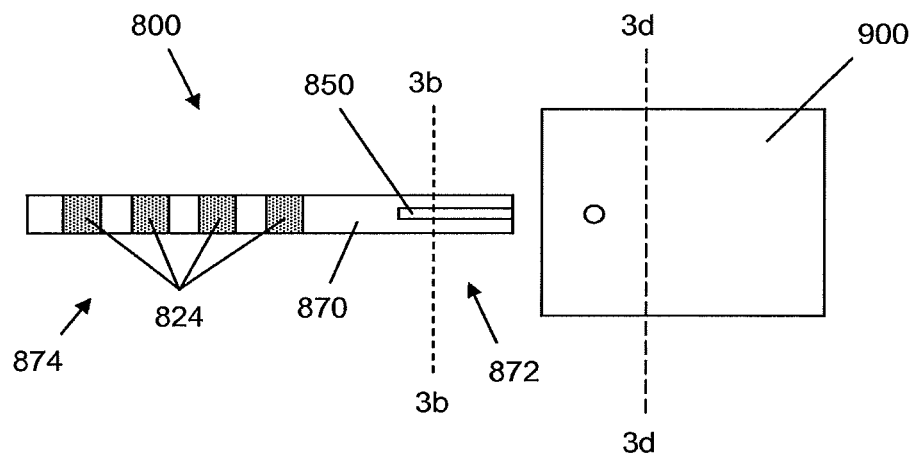
FIG. 3A is a schematic side view of a lead having an elongated contact and a connector configured to receive the lead.

Still referring to FIG. 3A, the elongate contact 850 is electrically coupled to an electrode 824 at the distal portion of the lead 800. The proximal portion 872 of the lead 800 may be inserted into a lead receptacle (not show in FIG. 3) of connector 900 to allow distal end and electrodes 824 of lead 800 to extend a variable distance from the connector 900 (e.g., as illustrated below with reference to FIGS. 5A-B).

Figure 3B:
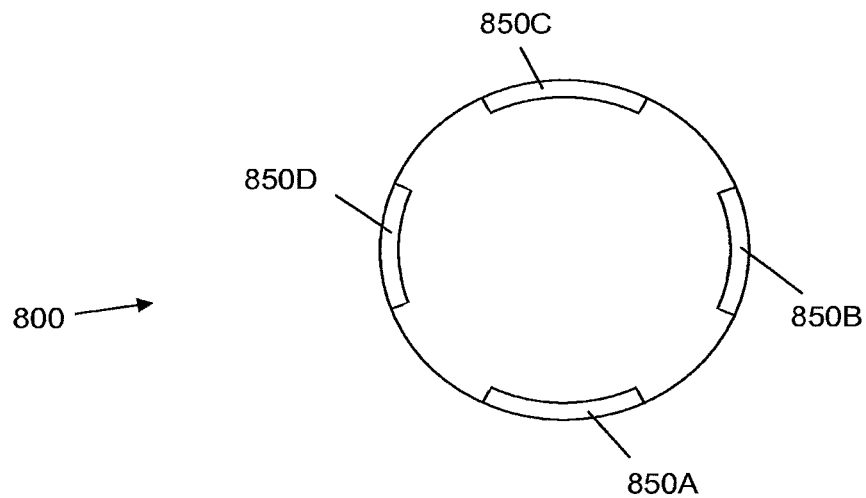
FIG. 3B is a schematic cross-section of the lead depicted in FIG. 3A taken through line 3*b*-3*b*.

Referring now to FIG. 3B, a cross section of lead 800 taken along line 3b-3b of FIG. 3A is shown. The depicted lead 800 includes four radially spaced apart contacts 850A. 850B, 850C, 850D, each of which may be electrically coupled to a distinct electrode 824 (see FIG. 3A). Of course a lead having radially spaced apart contacts 850 may include any suitable number of contacts and any suitable number of electrodes.

A lead having radially spaced apart contacts as described herein may be made in any suitable manner. One suitable manner for incorporating such contacts into a lead body is described in U.S. Published Patent Application 2006/0173262, entitled "Medical lead with segmented electrode", having application Ser. No. 11/343,667 filed Jan. 31, 2006, which published application is incorporated herein by reference in its entirety to the extent that it does not conflict with the disclosure presented herein. Contacts, as described herein, may be incorporated into a lead in a manner similar to the segmented electrodes in U.S. Published Patent Application 2006/0173262.

Figure 3C:
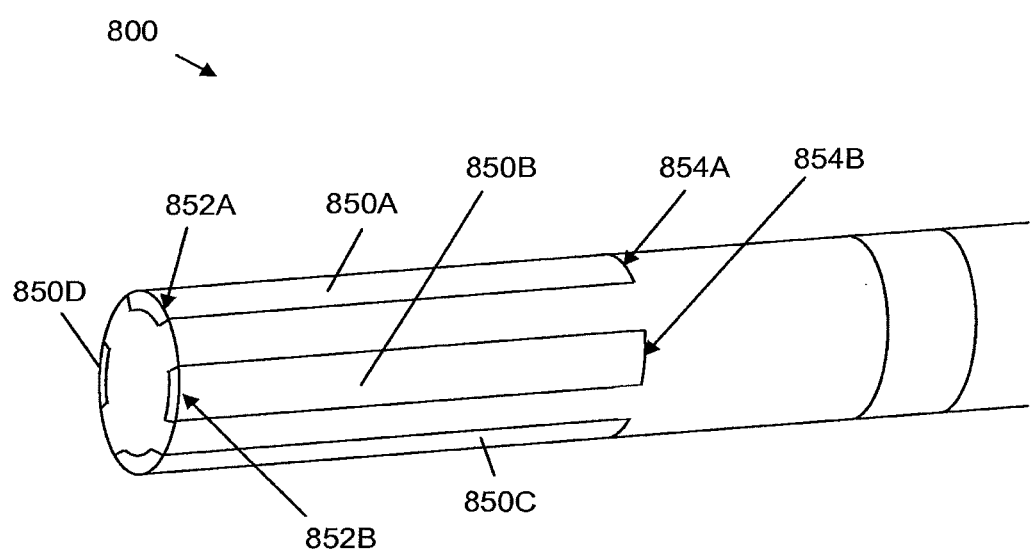
FIG. 3C is a schematic perspective view of an embodiment of a portion of the lead depicted in FIG. 3A.

Referring now to FIG. 3C, a perspective view of a portion of a representative lead 800 having a plurality of radially spaced apart contacts 850A, 850B, 850C, 850D is shown. The contacts 850A, 850B, 850C, 850D are elongate and have a proximal end 852A, 852B and a distal end 854A, 854B. The length of a contact 850A, 850B, 850C, 850D from the proximal end to the distal end may affect the adjustability of the lead 800. The longer the length of a contact, the more that the distance that the lead extends from the connector can be adjusted. The corresponding connector to which the lead is configured to be coupled should be modified to accommodate the length of the contact to achieve the full benefit of adjustability. In many cases, it may be desirable to keep the size of the connector small; e.g.

for ease of implantation or patient comfort. Thus, while a contact may be any length in theory, practical considerations may limit the length of the contacts of a lead. In various embodiments, the length of a contact less than about 10 cm. For example, the length of a contact may be between about 2 cm and about 10 cm, between about 1 cm and about 8 cm, between about 1 cm and about 5 cm, or about 2 cm.

Figure 3D:
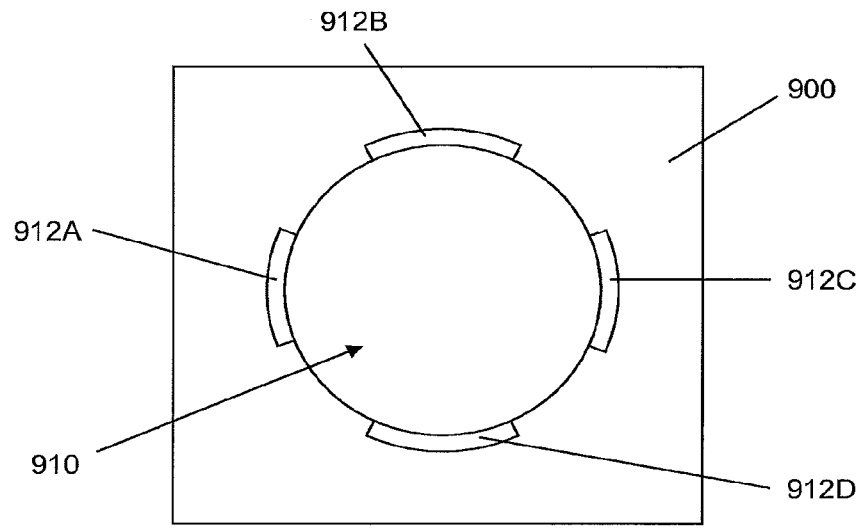
FIG. 3D is a schematic cross-section of the connector depicted in FIG. 3A taken through line 3*d*-3*d*.

Referring now to FIG. 3D, a cross-section of the connector shown in FIG. 3A taken at line 3d-3d is shown. The connector 900 includes a lead receptacle 910 configured to receive a lead. The lead receptacle 910 includes a plurality or radially spaced apart internal contacts 912A-D configured to electrically couple with radically spaced apart contacts of lead when the lead is inserted into the receptacle 910. Otherwise, the connector 910 may be similarly configured to connectors configured to receive leads having ring contacts.

Figure 4A:
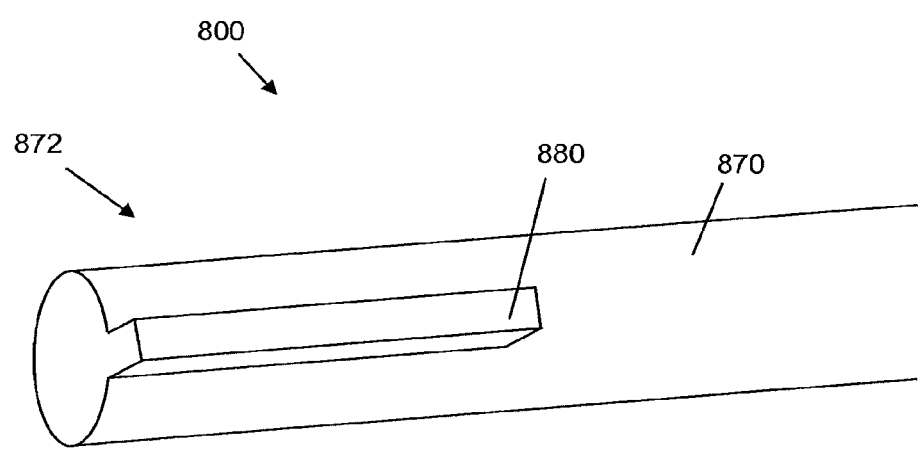
FIG. 4A is a schematic perspective view of a portion of a lead having a geometric feature for proper alignment within a connector.
Figure 4B:
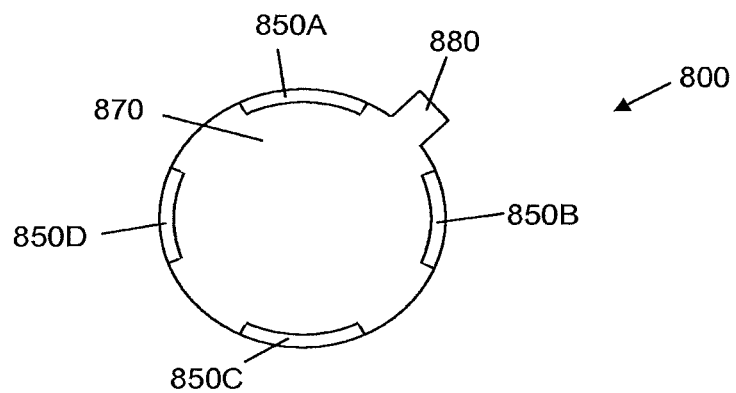
FIG. 4B is a head-on front view of the lead depicted in FIG. 4A.
Figure 4C:
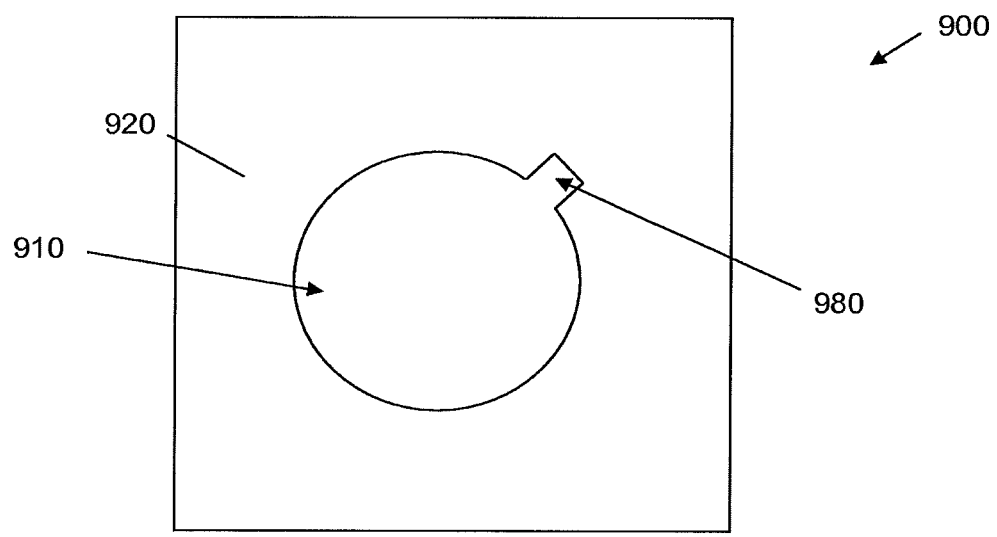
FIG. 4C is a head-on front view of a connector configured to receive the lead depicted in FIG. 4A.

Referring now to FIGS. 4A-C, a lead 800 and connector 900 may include encoding geometric features 880, 990 that assist in aligning the contacts 850A, 850B, 850C, 850D (not shown in FIG. 4A) of the lead 800 with internal contacts (not shown) of the connector 900. Any suitable encoding geometric features 880, 980 may be employed. For the purposes of illustration, the proximal portion 872 of the lead 800 depicted in FIG. 4A includes a protrusion 880 extending from the lead body 870. The protrusion 880 may be integrally formed with or otherwise affixed to the lead body 870, and may extend any suitable distance along the length of the lead 800. A head-on front view of the lead 800 is shown in FIG. 4B. A head-on front view of a connector 900 having a complementary geometric feature 980 to the geometric feature of the lead is shown in FIG. 4C. Preferably, the geometric feature 980 extends the internal length of the receptacle 910 of the connector 900.

In various embodiments, leads and connectors having radially spaced apart contacts are configured to allow the distance the lead extends from the connector to be adjusted. This will allow for adjustment of the position of the distal portion of the lead, and thus electrodes of the lead, to facilitate application of an electrical signal to the proper anatomical target, such as the occipital nerve.

Figure 5A:
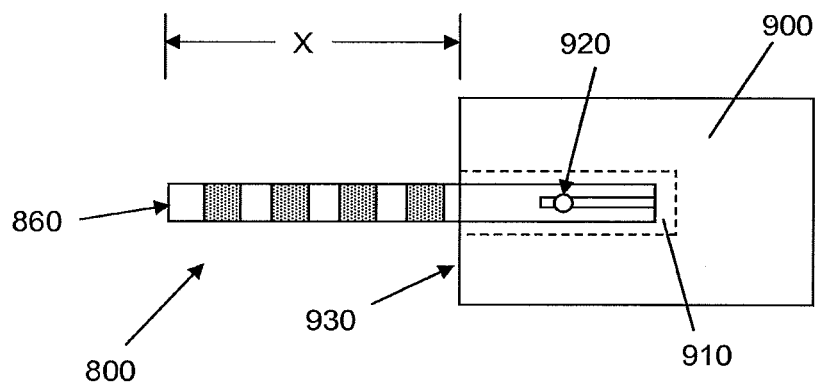
FIGS. 5A-B are schematic side views of lead having an elongated contact and a connector configured to receive the lead, showing the distance that the lead extends from the connector being adjustable.
Figure 5B:
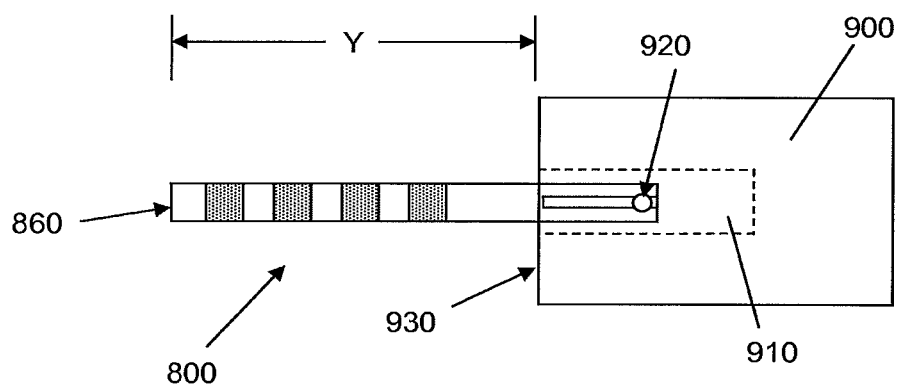

Referring now to FIGS. 5A-B, adjustment of the distance X, Y from face 930 of connector 900 in proximity to opening of lead receptacle 910 (dashed lines indicate that receptacle is internal) to distal end 860 of lead 800 is shown. As shown in FIG. 5B the distance Y that lead 800 extends from the face 930 of the connector is greater than the distance X depicted in FIG. 5A. For the purposes of illustration, the proximal end portion of the lead is shown extending into the connector. Once lead 800 is extended the appropriate distance, set screw 920 or other mechanism may be employed to secure lead 800 within lead receptacle and thus relative to face 930 of connector 900. If a set screw 920 is employed and if the set screw 920 is configured to assist in electrical coupling of a contact of the lead 800 to electronics of a medical device, the set screw 920 is preferably positioned at a location in the connector 900 to maximize the adjustability of the lead 800 (e.g., the set screw can engage the contact at the proximal or distal end of the contact, depending on how far the lead 800 is inserted into the receptacle 900). In addition, it may be desirable that the distal end of the contact 850 does not extend beyond the face 930 of the connector 900 in use. More particularly, it may be desirable for the contact 850 to be fully contained within the receptacle 910 in use. Seals or other features may be employed, in the connector 900 or on the lead 800, to electrically isolate the contact 850 from the body fluids of the patient when implanted.

The ability to adjust the length that a lead extends from a connector may be desirable in situations where excess lead length is undesirable. Typically, adjustability of the placement of a lead can be readily accomplished due to the presence of excess lead length. Once the lead is properly positioned, excess lead length can be wrapped or coiled and implanted in the patient. However, in some situations, it may not be desirable to have excess lead length. In such situations, leads with radially spaced apart contacts and corresponding connectors may allow for adjustments to provide proper lead placement without too much excessive lead length. One situation in which excess lead length may be undesirable is when the overall length of the lead is short and the lead is coupled to a connector in proximity to the intended site of action of the lead. Another situation in which excess lead length may be undesirable is when the excess coiled or wrapped lead would be implanted in a patient at a location that is uncomfortable for the patient or potentially harmful to the lead, such as in the neck or under the scalp.

Figure 6A:
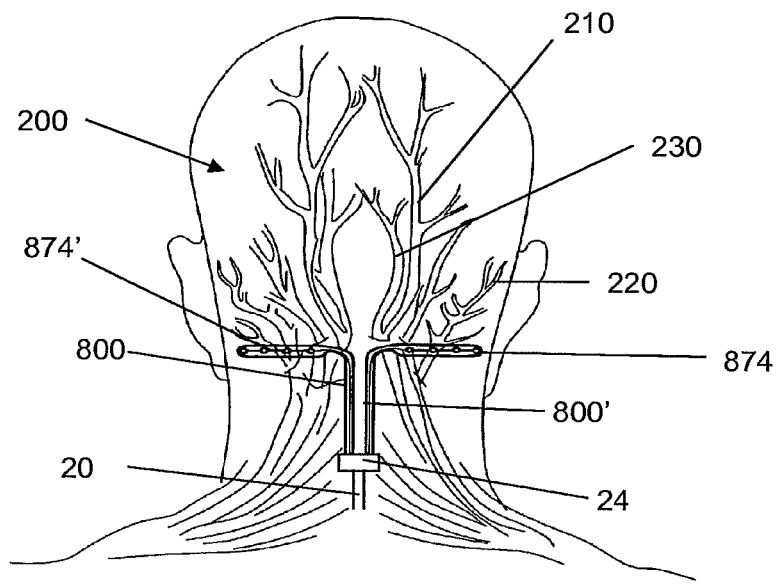
FIGS. 6A-B are schematic diagrams showing distal portions of bifurcated leads implanted in a subjects and positioned to apply an electrical signal to left and right occipital nerves.
Figure 6B:
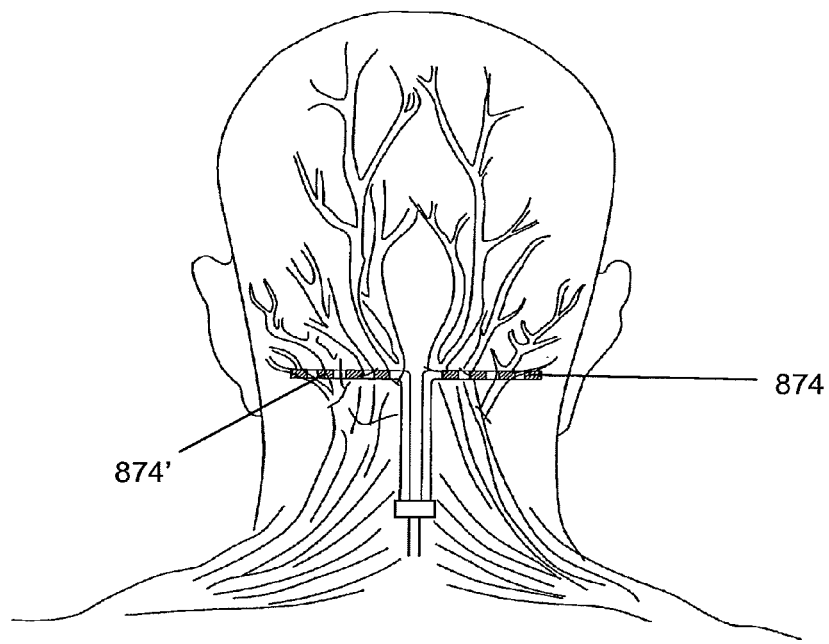

An example of such situations is depicted in FIGS. 6A-B, in which leads 800, 800' are positioned to apply an electrical signal to left and right occipital nerves 200 of a patient. In the embodiments depicted in FIGS. 6A-B, the leads 800, 800' are coupled to a connector 24 of a lead extension 20. A single lead extension 20 having a connector 24 capable of receiving two leads is tunneled to a location in proximity the patient's neck or base of the skull. Tunneling a single extension 20 (as opposed to two extensions) from a subcutaneous pocket into which an implantable signal generator is implanted reduces surgical time and potential complications. From this position in the neck or near the base of the skull, the leads 800, 800' may be connected to the extension 20 via the connector 24. The distance that the leads extend from the connector 24 may be adjusted as described above.

As used herein, "occipital nerve" includes the greater occipital nerve 210, the lesser occipital nerve 220 and the third occipital nerve 230. The greater and lesser occipital nerves are spinal nerves arising between the second and third cervical vertebrae (not shown). The third occipital nerve 230 arises between the third and fourth cervical vertebrae. The portion of the occipital nerve 200 to which an electrical signal is to be applied may vary depending on the disease to be treated and associated symptoms or the stimulation parameters to be applied. In various embodiments, the lead distal portions 874, 874' that contain electrodes are placed to allow bilateral application of electrical signals to the occipital nerve 200 at a level of about C1 to about C2 or at a level in proximity to the base of the skull. The position of the electrode(s) may vary. It will be understood that the electrode need not, and in various embodiments preferably does not, contact the nerve to apply the signal to the nerve. It will be further understood that a signal may be applied to any suitable portion of an occipital nerve, whether at a trunk, branch, or the like. In various embodiments, one or more electrodes are placed between about 1 cm and about 8 cm from the midline to effectively provide an electrical signal to the occipital nerve 200. Minor adjustments of the position of the electrodes relative to the occipital nerves 200 may be accomplished by moving the proximal portion of the lead within the connector 900. e.g. as described above with regard to FIGS. 5A-B.

As shown in FIG. 6A, the leads 800, 800' may include a paddle shaped distal portions 874, 874' containing electrodes. Such paddle shaped leads are often referred to as surgical leads. Examples of surgical leads that may be modified to form leads as described herein include Medtronic Inc.'s Resume, SymMix, On-Point, or Specify series of leads. Surgical leads typically contain electrodes that are exposed through one face of the paddle, providing directional stimulation. As shown in FIG. 6B, the leads may include distal portions 874, 874' that include electrodes that are generally cylindrically shaped. Such leads are often referred to percutaneous leads. Examples of percutaneous leads that may be modified to form leads as described herein include Medtronic Inc.'s Quad Plus, Pisces Quad, Pisces Quad Compact, or 1×8 SubCompact, 1×8 Compact, and 1×8 Standard leads. Such percutaneous leads typically contain ring electrodes that apply an electrical stimulation signal to tissue in all directions around the ring. Accordingly, the amplitude of the signal (and thus the energy required from the signal generator) applied may be greater with percutaneous leads that surgical leads for occipital nerve therapies.

Figure 7:
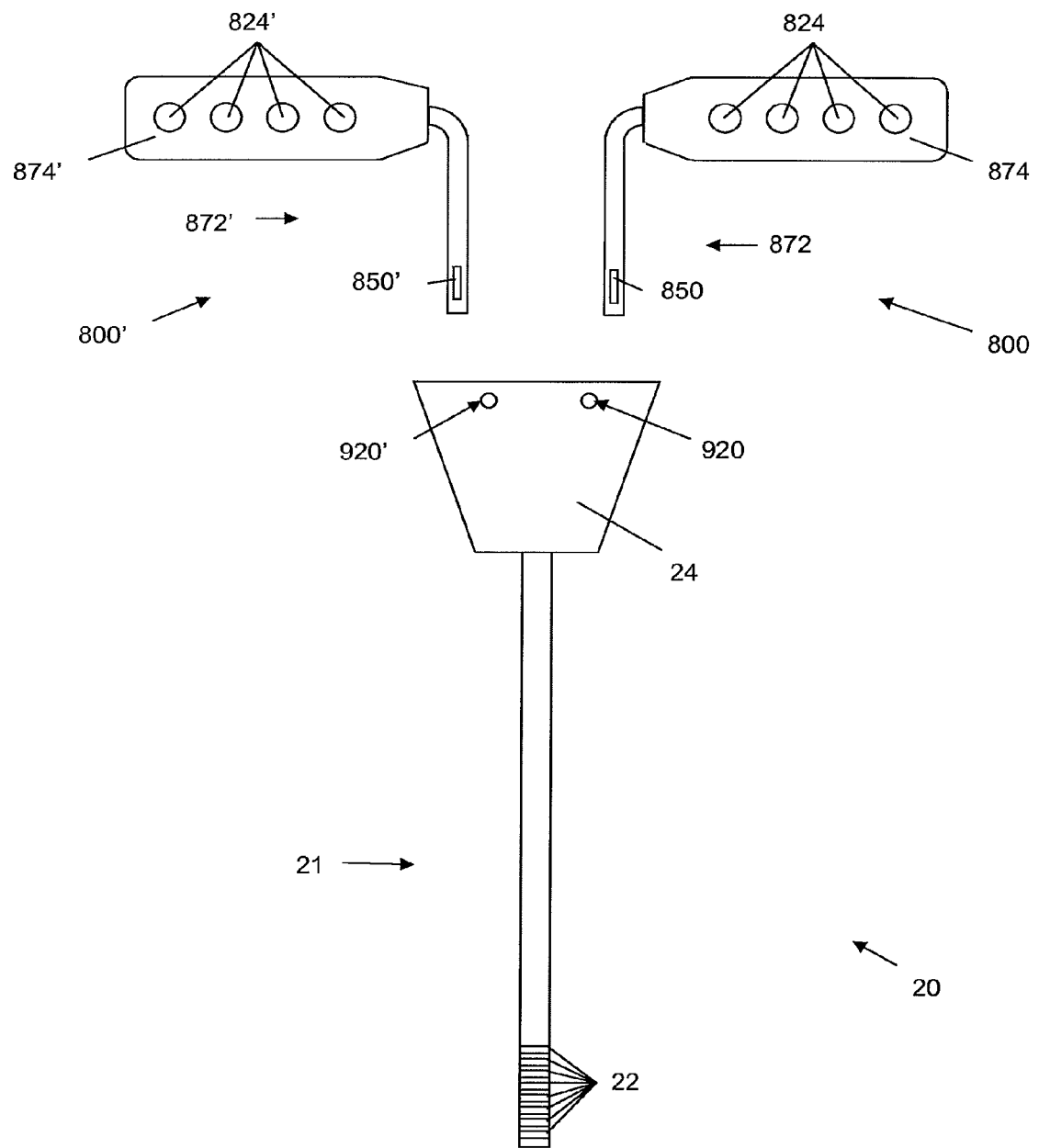
FIGS. 7-8 are schematic side views of lead extensions having bifurcating connectors and associated leads.
Figure 8:
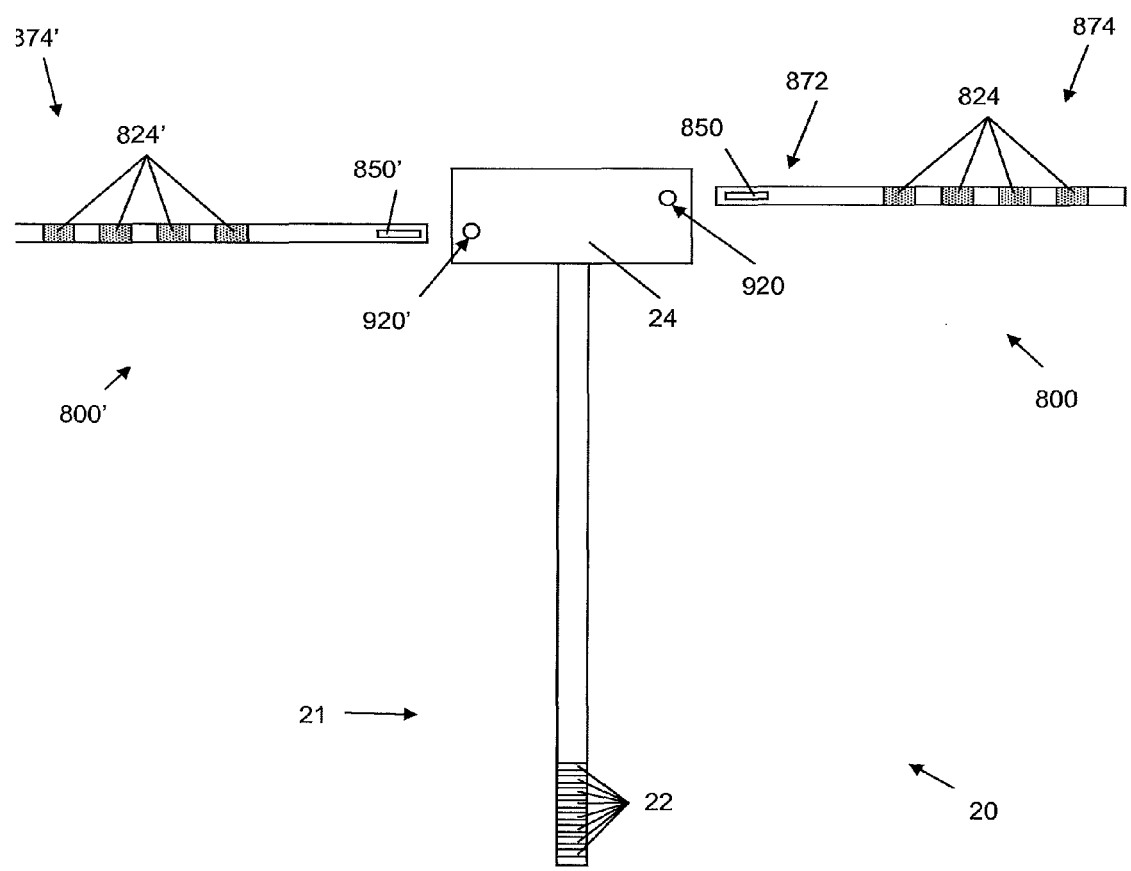

Schematic drawings of some representative leads 800, 800' having elongate radially spaced apart contacts 850, 850' and extensions 20 that may be employed to apply electrical signals to occipital nerves as described above are shown in FIGS. 7-8. In the depicted embodiments, the proximal portion 21 of the extension 20 includes contacts 22 for electrical coupling the extension 20 to a signal generator. The distal portion of extension 20 includes a connector 24 containing two lead receptacles (not shown) having internal contacts for coupling to contacts 850, 850' of leads 800, 800'. The connector 24 may be of any suitable size and shape. In various embodiments, the connector 24 has a volume of less than about 10 cubic centimeters; e.g., less than about 5 cubic centimeters. Set screws 920, 920' may be used to secure leads 800, 800' in receptacles. Of course, any other suitable mechanism for securing leads 800, 800' in receptacles may be employed. In the embodiment depicted in FIG. 8, the lead receptacles (not shown) are generally perpendicular to the angle of entry of the proximal portion 21 into connector 24.

Leads 800, 800' include proximal portions 872, 872' containing contacts 850, 850' and distal portions 874, 874' containing electrodes 824, 824'. In many embodiments, the number of contacts 22 of the extension 20 is equal to the total number of electrodes 824, 824' of both of the leads 800, 800', and each receptacle (not shown) of the connector 24 has a number of contacts corresponding to the number of contacts 850, 850' of the lead 800, 800' that the receptacle is configured to receive.

Various embodiments of leads, connectors, devices or systems have been described above with regard to occipital nerve stimulation. However, it will be understood that such leads, devices and systems may be used for any other therapeutic or monitoring purpose. It will be further understood that leads and connectors as described herein may or may not be used in configurations where the distance the lead extends from the connector is adjustable.

Thus, embodiments of LEAD HAVING RADIALLY SPACED APART CONTACTS TO ALLOW FOR ADJUSTABILITY are disclosed. One skilled in the art will appreciate that the leads, extensions, connectors, devices such as signal generators, systems and methods described herein can be practiced with embodiments other than those disclosed. The disclosed embodiments are presented for purposes of illustration and not limitation.

What is claimed is:

1. A method for adjusting the distance from which a lead extends from a face of a connector configured to receive the lead, the connector including a lead receptacle having first and second internal contacts configured to electrically couple to the first and second contacts of the lead, the method comprising:

inserting a lead into the lead receptacle, the lead comprising
  a lead body having a proximal portion and a distal portion, the proximal portion having a proximal end, and the distal portion having a distal end,
  first and second contacts located at the proximal portion of the lead body, and
  first and second electrodes located at the distal portion of the lead body, wherein the first electrode is electrically coupled to the first contact and the second electrode is electrically coupled to the second contact,
  wherein the first contact has a proximal end and a distal end and the second contact has proximal end and a distal end, and
  wherein the second contact is radially spaced apart from the first contact; and
a device having a lead connector configured to receive the lead, wherein the connector has first and second radially spaced apart internal contacts, wherein the first internal contact is configured to engage and electrically couple the first contact of the lead when the lead is received by the connector, and wherein the second internal contact is configured to engage and electrically couple the second contact of the lead when the lead is received by the connector;
wherein the lead is axially moveable in the connector such that the distance the lead extends from a face of the connector is adjustable, and wherein the first and second contacts of the lead and the first and second contacts of the connector, respectively, are electrically couplable at a plurality of axial positions as the lead is moved axially within the connector; and
adjusting the distance that the lead extends from the face of the connector by axially moving the lead within the lead receptacle, wherein the first and second contacts of the lead are capable of electrically coupling to the first and second internal contacts of the receptacle as the lead is being axially moved within the receptacle.

2. A method according to claim 1, wherein the connector is included in an electrical signal generator.

3. A method according to claim 1, wherein the connector is included in a lead extension.

4. An implantable medical device, comprising:
  a lead connector configured to receive a lead having radially spaced apart first and second contacts, wherein the connector has first and second radially spaced apart internal contacts, wherein the first internal contact is configured to engage and electrically couple the first contact of the lead when the lead is received by the connector, and wherein the second internal contact is configured to engage and electrically couple the second contact of the lead when the lead is received by the connector;
  wherein device is configured to allow the lead to move longitudinally in the connector such that the distance the lead extends from a face of the connector is adjustable, and wherein the first and second contacts of the lead and the first and second internal contacts of the connector, respectively, are electrically couplable at a plurality of axial positions as the lead is moved longitudinally within the connector.

5. A device according to claim 4, wherein the connector is configured to allow insertion of the lead, wherein the distance from a proximal end of the first contact of the lead to a distal end of the first contact of the lead is between 2 cm and 10 cm, and wherein the distance from a proximal end of the second contact of the lead to a distal end of the second contact of the lead is between 2 cm and 10 cm.

6. A device according to claim 4, wherein the connector is configured to allow insertion of the lead, wherein the distance from a proximal end of the first contact of the lead to a distal end of the first contact of the lead is about 2 cm, and wherein the distance from a proximal end of the second contact of the lead to a distal end of the second contact of the lead is about 2 cm.

7. A device according to claim 4, wherein the device is an implantable signal generator.

8. A device according to claim 4, wherein the device is an implantable lead extension.

9. A device according to claim 8, further comprising an implantable signal generator configured to be coupled to the lead extension such that a signal generated by the signal generator may be transmitted to an electrode of the lead via the lead extension.

* * * * *